(12) United States Patent
Winicov

(10) Patent No.: US 6,936,708 B1
(45) Date of Patent: Aug. 30, 2005

(54) EXPRESSION OF ALFIN 1 AND METHODS FOR PRODUCING TRANSGENIC PLANTS HAVING INCREASED ROOT GROWTH AND ROOT SPECIFIC GENE ACTIVATION

(75) Inventor: Ilga Winicov, Scottdale, AZ (US)

(73) Assignee: Arizona Board of Regents, acting for and on behalf of Arizona State University, Tempe, AZ (US)

( * ) Notice: Subject to any disclaimer, the term of this patent is extended or adjusted under 35 U.S.C. 154(b) by 0 days.

(21) Appl. No.: 09/647,841

(22) PCT Filed: Apr. 8, 1999

(86) PCT No.: PCT/US99/07902

§ 371 (c)(1),
(2), (4) Date: Oct. 5, 2000

(87) PCT Pub. No.: WO99/53016

PCT Pub. Date: Oct. 21, 1999

Related U.S. Application Data

(60) Provisional application No. 60/081,348, filed on Apr. 9, 1998, and provisional application No. 60/128,083, filed on Apr. 7, 1999.

(51) Int. Cl.$^7$ .............................................. C12N 15/11
(52) U.S. Cl. ...................................... 536/24.1; 800/287
(58) Field of Search ........................ 536/24.1; 800/287, 800/278, 298; 435/468

(56) References Cited

PUBLICATIONS

Oommenn et al (1994, The Plant Cell 6:1789–1803).*
Kagaya et al (1995, Mol. Gen. Genet. 248 :668–674).*
John W. Schiefelbein, Building a Root: The Control of Patterning and Morphogenesis during root Development, The Plant Cell, Jul. 1997, 1087–1098, vol. 9, American Society of Plant Physiologists.
Wout Boerjan, supperroot, a Recessive Mutation in Arabidopsis, Confers Auxin Overproduction, The Plant Cell, Sep. 1995, 1405–1419, vol. 7, American Society of Plant Physiologists.
Robert A. Creelman, Water Deficit and Abscisic Acid Differential Inhibition of Shoot versus Root Growth in Soybean Seedlings, Plant Physiol., 1990, 205–214, vol. 92.
Raul B. Larson, Al Inhibits Both Shoot Development and Root Growth in als3, an Al–Sensitive Arabidopsis Mutant, Plant Physiol., 1997, 1201–1214, vol. 114.
M.R. Foolad, Mapping salt–tolerance genes in tomato (Lycopersicon esculentum) using trait–based marker analysis, Theor Appl Genet, 1993, 184–192, vol. 87.
Ilga Winicov, cDNA Encoding Putative Zinc Finger Motifs from Salt–Tolerant Alfalfa (*Medicago sativa* L.) Cells, Plant Physiol., 1993, 681–682, vol. 102.
Ce Deutch, Post–transcriptional regulation of a salt–inducible alfalfa gene encoding a putative chimeric proline–rich cell wall protein, Plant Mol Biol., 1995, (Abstract Only).

Ilga Winicov, Transgenic Overexpression of the Transcription Factor Alfin 1 Enhances Expression of the Endogenous MsPRP2 Gene in Alfalfa and Improves Salinity Tolerance of the Plants Plant Physiology Jun. 1999 473–480, vol. 120.
Dhundy R. Bastola, Alfin 1, a novel zinc–finger protein in alfalfa roots that binds to promoter elements in ;the salt–inducible MsPRP2 gene, Plant Molecular Biology, 1998, 1123–1135, vol. 38 Kluwer Academic Publishers Netherlands.
FJ Rauscher 3rd, Binding of the Wilms' tumor locus zinc finger protein to the EGR–1 consensus sequence, Science, Nov. 1990, 1259–1262, vol. 4985 (Abstract Only).
Yuri T. Yamamoto, Characterization of cis–Acting Sequences Regulating Root–Specific Gene Expression in Tobacco, The Plant Cell, Apr. 1991, 371–382, vol. 3, American Society of Plant Physiologists.
E. Adam, Transcription of tobacco phytochrome–A gene initiates at multiple start sites and requires multiple cis–acting regulatory elements, plant Mol Biol., Dec. 1995, 983–993, vol. 29(abstract only).
GA Mignery, Molecular characterization of the patatin multigene family of potato, Gene, 1988, 27–44, vol. 62(1). (abstract only).
F. Sato, Ethylene–induced gene expression of osmotin–like protein, a neutral isoform of tobacco PR–5, is mediated by the AGCCGCC cis–sequence, Plant Cell Physiol., Apr. 1996 249–255 vol. 37(3) (abstract only).

* cited by examiner

*Primary Examiner*—Amy J. Nelson
*Assistant Examiner*—Stuart F. Baum
(74) *Attorney, Agent, or Firm*—Needle & Rosenberg, P.C.

(57) ABSTRACT

Alfin1 cDNA encodes a putative transcription factor associated with salt tolerance in alfalfa (*Medicago sativa* L.). The recombinant protein binds DNA in a sequence specific manner, including promoter fragments of the salt inducible gene MsPRP2. Alfin1 function was tested in transgenic alfalfa under the control of the 35S promoter in the sense and antisense orientations with the endogenous MsPRP2 as a reporter gene. Calli overexpressing Alfin1 were more resistant to growth inhibition by 171 mM NaCl than vector transformed controls, while calli expressing Alfin1 antisense were more sensitive to salt inhibition. Transgenic plants overexpressing Alfin1 in the sense orientation grew well. In contrast, the antisense transgenic plants grew poorly in soil, demonstrating that Alfin1 expression is essential for normal plant development. Transgenic calli and plant roots overexpressing Alfin1 showed enhanced levels of endogenous MsPRP2 mRNA accumalution. However, MsPRP2 mRNA accumulation was also regulated in a tissue specific manner as shown in leaves of transgenics overexpressing Alfin1. These results suggest that Alfin1 acts as a transcriptional regulator in plants and MsPRP2 expression in alfalfa. Alfin1 overexpressing transgenics showed salinity tolerance comparable to one of our salt-tolerant plants, indicating that Alfin1 also functions in gene regulation in salt tolerance.

1 Claim, 9 Drawing Sheets

This is Alfin cDNA sequence of the clone as submitted to GenBank #L07291

GAATTCCCTTGACTTTTGTTGAAATTGAGGATGGAAGGAATGGCACAGCACCCA
GTACCTCGAACTGTTGAAGAAGTTTTTAGCGATTACAAAGGCAGACGCGCCGGT
TTGATCAAAGCTCTCACTACTGACGTTGAAAAGTTTTACCAGCTCGTCGATCGC
GAAAAGGAGAATTTGTGCCTCTATGGGTTTCCAAATGAAACATGGGAAGTGAAC
TTGCCTGTTGAGGAAGTGCCTCCTGAACTTCCCGAGCCAGCATTGGGTATAAA
CTTTGCTCGGGATGGAATGCAGGAGAAGGACTGGTTATCACTGGTTGCAGTTC
ACAGTGACTCATGGCTGCTCGCTGTTGCTTTCTATTTTGGTGCCCGCTTTGG
ATTTGGTAAGAATGATAGGAAAAGGCTTTTTCAGATGATAAATGA
TCTGCCCACAGTCTTTGAGCTTGCAACAGGAACTGCTAAGCAATCAAACGAC
CAACTGACTGCTCACAACAATGGTAGCAATAGCAAATACAAATCAAGTGGAAAGT
CCCGCCAGTCTGAATCCCAGACCAAGGGTGTGAAGATGTCTGCACCGGTCAAAG
AAGAGGTTGACAGTGGAGAAGAAGAGGAAGAAGATGATGATGAACAAGGTGCAAC
CTGTGGTGCTTGTGGTGATAATTATGGCACCGATGAATTCTGGATCTGTTGT
GATATGTGCGAGAAATGGTTCCATGGTAAATGTGTTAAAATTACTCCTGCCAAG
GCTGAACACATCAAGCAATACAAGTGCCCTGGCTGCAGTATCAAGAAGCCAAGAA
TTGGATAGCTCTGAACGTTTGGACCATTAGCGGGCAAGATTAAAATGTTTGTTA
GCATTTCTGTAAGTGAAACCATTGTTGTCTGCATAGTCACTTAAAGGGAATTCC

FIG. 1A

DNA Sequences that bind Alfin *in vitro*

| Clone | Sequence | |
|---|---|---|
| | 5'primer | Insert |
| 6 | 5'GACG- | GCTGGGGGAAAGTGA<u>GCGGT</u>GGCCC 3' |
| 7* | GACG- | CAAAG<u>GGGGTGGGG</u>ACGGCGCTTTT |
| 18* | GACG- | CAAAG<u>GGGGTGGGG</u>ACGGCGCTTTT |
| 15 | GACG- | GGTAG<u>GGTGTGGGGGGT</u>GTTTTATT |
| 16 | GACG- | GGGATA<u>GGTGAGGTGGAGG</u>GACAAT |
| 22 | GACG- | GCAGAAGGGAGAAA<u>CGTGG</u>AGAATC |
| 25 | GACG- | GCGGGAAGGA<u>GTGTGG</u>TAGAGAGCC |
| 21 | GACG- | AAGGAAGGAC<u>GGCAGCGTG</u>TTGC |
| 5 | GACG- | AAAANTTANAN<u>GTGTAGGTGGG</u>ACT |

\* - individual isolates

Consensus: 2-5 Triplets bordered by G and containing at least one GTG, most conforming to the high affinity Zif268 binding sites

MsPRP2 Fragments

| 211 | coding | 5'  -299 GT<u>GT</u>GGGGCCC -289 |
| | non-coding | 5'  -390 AAA<u>GT</u>GGGGCA -398 |
| 218 | non-coding | 5'  -826 GAT<u>GTGTGTGT</u>GTTC -838 |
| 187 | non-coding | 5'  -504 CAA<u>GTGGTGCTG</u> -515 |
| | non-coding | 5'  -463 AAA<u>GCGGTGCTG</u> -414 |

FIG. 2

```
TTTTATAAATATTTAAGCTTGATAATAATTTTTGCGATCTATATATAAGCCAC-1501

TACCAATTTAAAATTATATATATATATATATATATATATATATATAATAATTTTTATT-1441

ATATTTATTACGTTGATGGTAAAAAAATAAATATAATTTGTTACCATTTAAAAGTCATAA-1381

ATATAGTACAATCCAACCCTTTGAGAGGTTAATGTGTGTGCGGATTTTCTAGATAAACAA-1321

GGTGCCATTCACGATTCTTCTTGGTGCAGCTTGGAGAACCCTATCCTGGGCTTGGAAGAT-1261

TTACTTCTTGTTGATGCTTCTAGAGTACAGCTCCTTAAGGCTGTAGTCTAGTTTTTTTTT-1201

TCATCCTTCCTACCAAAAAAAAAAAAGTCATAAATATAGTTTATACATATAACTTTAATA-1141

AAAATAAAAAAATTTCATCCCTAAAAACATAGTAGAAATTTCATAAAAAAAATATTGTTT-1081

ATAATTTACATGCCCGTTACCGTAAAAAATGGATAAATTGGGTATGGAGTACTAGTAATTA-1021

ATAAGGTTCATTGGTTAAAAAAACTAAAAAATAATTTCTCTCCTGATTTATATGAAATGA- 961

CATTTTTTTGGAACATGAAGGGTATTGATTTTTACCACCTTTTACACCTTTCAAAGCCAT- 901

TCAAGGATGAATATAGATTTTTGGGCGATCAAACACAAGAATCATTACGATAACATGCTT- 841
                                        TfiI
TGGAACACACACATGCTTAAATTAATGGTTGGAGTATCAAATTTTAAAATATTGTTGTCA- 781
   Alfin1*/myc        myb*
ATACATACCCCGTCAATCTTCTTTTTTTTTACCCAATAAACATTGAAATGTTGCTTCTTTC- 721
   Alfin1*
GTTAAGCATAAAAACATCAAAGTCTAGCAAAATGTTGTTTTTGCGATGACACATTTCATA- 661

TAGTTTAAAGGATGCATGATTCGATTACAAAAACAAAATACTAATAATTCTAGCACAAAG- 601
                 TfiI
TTTAAAGCAAGATTATAAAGCTTCATAGCATGTGGATATTCATTTAGAAATATAGATTAG- 541
                        myc
ATTGCCCCTTTCATCACGGGTCTAACAGCACCACTTGTCAGTACATGTCAAAAATGTCCT- 481
                    myb/Alfin1*/myc
CTAGTACAGCACCGCTTTTTACTTGATTCCCCTTGTCCATGCATGAAAAAAATCAAAACA- 421
      Alfin1*         TfiI
ATATTTGGACACACAAACTTGCCCCCACTTTCCTTTTTCTTTCTGCCCTAGTTTGTTTGA- 361
              Alfin1*
GACTCATATTGATCAAATTTGGCTATGAATTCAAACAAAAAATTCACTCTACCCATTGCA- 301
                                                        myc\
TGTGTGGGGCCCACATATAAATCCATGAAGGATTTCAATGTCCATCGAAGTCAATGATTC- 241
Alfin1                                              TfiI
AACATATATAACATTGAATAATTTAATTCCAATTTGCAGTATTATGATTTAGATTGATTG- 181

CTGCAATACGGTCCGTCAATGTGATCACTCACGAGAAAGAGGTATCAAAATTTCAAGGTA- 121

TTTTATTTATTTTTAACAAATAAAATTTCAAGGTGTTGTTCACCATATAAACCTCCTCAC- 61

TCACACCCAATTCTCTTAAGTGTATGACTTCATAGTACACTACACTAGTTTCTTTGAAAC- 1

ATGGCTAACTATGCTCTAGCCAATGTTTTCATCCTTCTCTTGAACTTGAGTACCTTACTC+ 60
Met
```

FIG. 3

CALLUS

EXPRESSION OF ALFIN 1 AND METHODS FOR PRODUCING TRANSGENIC PLANTS HAVING INCREASED ROOT GROWTH AND ROOT SPECIFIC GENE ACTIVATION

This application is a National Stage of International Application No. PCT/US99/07902, filed on Apr. 8, 1999, under 35 U.S.C. §371, which claims the benefit under 35 U.S.C. 119(e) of U.S. Provisional Application 60/128,083, filed Apr. 7, 1999, and U.S. Provisional Application 60/081,348, filed Apr. 9, 1998.

FIELD OF THE INVENTION

This invention relates to the use of Alfin1 gene for the production of transgenic plants having increased root production, increased expression of root specific genes, and general growth. The unexpected vigor of transgenic plants using Alfin1 transgene and a root specific promoter from the MsPRP2 gene (containing Alfin1 DNA binding sites) which is regulated by Alfin1, are described in detail.

BACKGROUND ART

Plant roots are organs adapted to accumulate water and nutrients from the soil and to provide these necessary ingredients for optimal growth and development of the entire plant. Plant roots also carry out specialized functions that contribute to overall plant yield and in case of root or tuber crops, constitute the essential plant yield. Root growth and development have been reviewed (See: Aeschbacher, R. A, Schiefelbein, J. W. and Benfey, P. N. *The Genetic and Molecular Basis of Root Development*. Annu. Rev. Plant Physiol. Plant Mol. Biol., 1994, 45, 25–45; Schiefelbein, J. W., Masucci, J. D. and Wang, H. *Building a Root: The Control of Patterning and Morphogenesis During Root Development*. Plant Cell 9, 1997, 1089–1098). While meristem maintenance and proliferative growth of roots is determined by cell cycle regulation and cyclin expression or plant hormones such as ethylene and auxin can enhance root growth (See: Boerjan, W., Cervera, M. T., Delarue, M., Beeckman, T., Dewitte, Wl, Bellini, C., Caboche, M., Van Onckelen, H., Van Montagu, M. and Inze, D. *Superroot, A Recessive Mutation in Arabidopsis, Confers Auxin Overproduction*. Plant Cell 7, 1995, 1405–1419) additional regulatory factors appear also to be necessary for new root growth.

Root encounters with soil environmental conditions determine plant productivity and a well developed root system functions in nutrient and water uptake and determines to a significant extent plant yield. The function of the roots is profoundly influenced by soil nutrient composition and any toxins as well as abiotic and biotic environmental stress. Thus, inhibition of shoot growth with continued root growth has been considered as a morphological adaptation to water stress or salt stress (See: Creelman, R. A., Mason, H. S., Bensen, R. J., Boyer, J. S. and Mullet, J. E. *Water deficit and abscisic acid cause differential inhibition of shoot versus root growth in soybean seedlings*. Plant Physiol., 1990; 92, 205–214). Increased root mass may also play an important defensive role in metal toxicity, since reduced shoot expansion and yield are considered to be secondary from inhibition of root growth and nutrient accumulation (See: Larsen, P. B., Kochian, L. V. and Howell, S. H. *Al Inhibits both shoot development and root growth in als3, an Al-sensitive Arabidopsis mutant*. Plant Physiol., 1997, 114, 1207–1214). Improved root growth and development thus can enhance overall plant productivity and appears to be a desirable trait for manipulation in plants.

The present work is an outgrowth of early efforts to develop crop plants with improved salt tolerance that included the regeneration of plants after selection of salt-tolerant cells in culture (See: Winicov, I. *Characterization of salt tolerant alfalfa (Medicago sativa L plants regenerated from salt tolerant cell lines*. Plant Cell Reports, 1991; 10, 561–564; Winicov, I. *Characterization of rice (Oryxa sativa L) plants regenerated from salt-tolerant cell lines*. Plant Sci., 1996; 113, 105–111) coupled with identification of genes differentially regulated in the salt tolerant cells and plants (See: Winicov, I. and Bastola, D. R. *Salt tolerance in crop plants: New approaches through tissue culture and gene regulation*. Acta Physiol. Plant., 1997; 19, 435–449). Transgenic plants have been constructed in a number of other laboratories to over-express single genes, known to be up-regulated by salt/drought stress in prokaryotes or plants (See: Holmberg, N. and Bulow, L. *Improving stress tolerance in plants by gene transfer*. Trends in Plant Sci., 1998; 3, 61–65). However, the molecular mechanisms by which plants can acquire improved long term salt tolerance and maintain their productivity are still not understood and may involve the regulation of many genes (See: Winicov, I. *New molecular approaches to improving salt tolerance in crop plants*. Annals of Botany 1998; 82, 703–710), since salt tolerance has been considered to be a quantitative trait (See: Foolad M. R., Jones R. A. *Mapping salt-tolerance genes in tomato (Lycopersicon esculentum) using trait-based marker analysis*. Theor. Appl. Genet., 1993; 87, 184–192). Thus, the identification of regulatory genes that can influence the expression of other genes in a specific manner could be particularly useful in manipulating not only plant growth, but also enhance their tolerance to a variety of biotic and abiotic environmental stress conditions.

DISCLOSURE OF INVENTION

Several gene transcripts have been cloned which are enhanced in the salt-tolerant alfalfa cells and also are salt induced at the mRNA level in whole plants. The present disclosure focuses on two particularly interesting and novel isolates. One is Alfin1, which encodes a putative zinc-finger regulatory protein (See: Winicov, I. *cDNA encoding Putative zinc finger motifs from salt-tolerant alfalfa (Medicago sativa L.) cells*. Plant Physiol., 1993; 102, 681–682.). The other is MsPRP2, a single copy gene, which encodes a proline-rich protein with a hydrophobic cysteine-rich carboxy terminus that could serve as a linker molecule between the cell wall and the membrane (See: Winicov, I. and Deurch, C. E. *Characterization of a cDNA clone from salt-tolerant alfalfa cells that identifies salt inducible root specific transcripts*. J. Plant Physiol., 1994; 144, 222–228; Deutch, C. E. and Winicov, 1. *Post-transcriptional regulation of a salt-inducible alfalfa gene encoding a putative chimeric proline-rich cell wall protein*. Plant Mol. Biol., 1995; 27, 411–418). Interestingly, both of these genes are expressed primarily in roots and MsPRP2 is strongly salt inducible upon continued growth of the plants in 87 or 171 mM NaCl. Alfin1 is a unique gene in the alfalfa genome and appears to be conserved among diverse plants, including rice and *Arabidopsis* (See: Winicov, I. and Bastola, D. R. *Salt tolerance in crop plants: new approaches through tissue culture and gene regulation*. Acta Physiol. Plant., 1997; 19, 435–449; Winicov, I. and Bastola, D. R. *Transgenic over-expression of the transcription factor Alfin1 enhances expression of the endogenous MsPRp2 gene in alfalfa and improves salinity tolerance of the plants*. Plant Physiol., 1999; (in press).

Accordingly, a principal object of the present invention is to enhance the production of transgenic plants having increased root production and general growth. Another object of the present invention is to enhance the vigor of transgenic plants using Alfin1 transgene and a root specific promoter from the MsPRP2 gene (which is influenced by Alfin1) to enhance overall plant yield.

These and still further objects as shall hereinafter appear are readily fulfilled by the present invention in a remarkably unexpected manner as will be readily discerned from the following detailed description of an exemplary embodiment thereof especially when read in conjunction with the accompanying drawings in which like parts bear like numerals throughout the several views.

BRIEF DESCRIPTION OF THE DRAWINGS

In the drawings:

FIG. 1A shows the sequence of Alfin1 cDNA (GenBank accession number L07291) (SEQ ID NO:2).

FIG. 2 shows the DNA sequences that bind Alfin1 in vitro (SEQ ID NOS: 3–11)

FIG. 3 shows the MsPRP2 genomic region in *M. sativa* (Gen Bank accession number AF 028841) (SEQ ID NO: 1).

BEST MODE FOR CARRYING OUT THE INVENTION

Figure 1B:
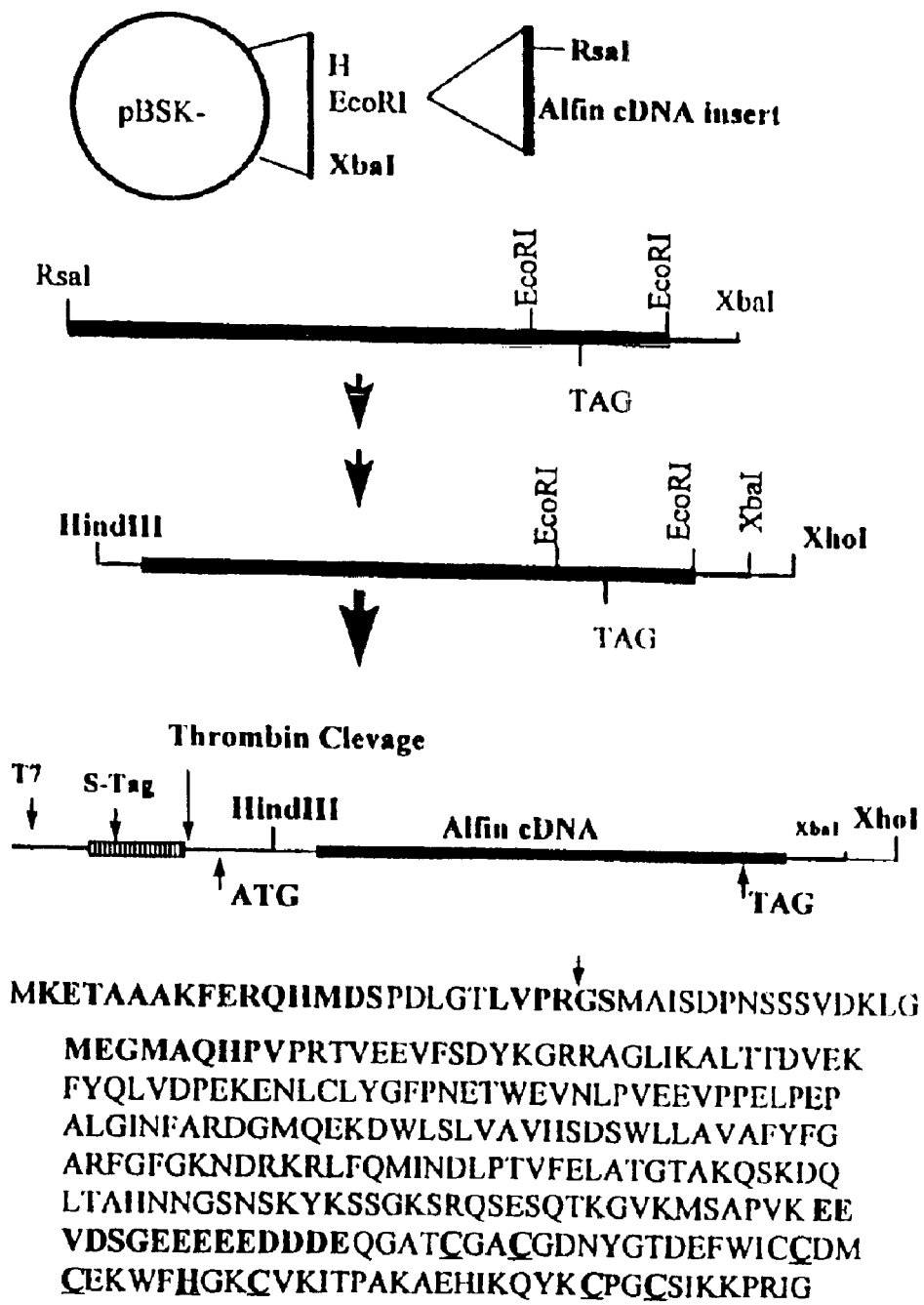
FIG. 1B shows the expression of Alfin1 fusion protein in *E. coli*.

Since Alfin1 cDNA was cloned by differential screening, the function of Alfin1 as a potential regulatory factor in plant roots was not known and needed to be demonstrated. See FIG. 1, in which the Alfin1 cDNA sequence (SEQ ID NO: 2) and deduced amino acid sequence are shown. Cys and His residues comprising the putative zinc finger are underlined. Dashed line indicates strongly acidic region of the protein. If Alfin1 were to act as a transcription factor in root specific regulation, DNA binding of the protein might be expected. To test for sequence specific DNA binding, recombinant Alfin1 protein was first expressed in *Escherichia coli* from the construct shown in FIG. 1B, in which the schematic representation of the pET-29b construct for Alfin1 fusion protein is shown. The top line of the amino acid sequence shos the S-Tag and the biotinylated thrombin cleavage site of the vector. The Alfin1 sequence below shows in bold the nine N-terminal amino acids deleted in the construct, the negatively charged region and the hputative zinc binding domain with the relevant $Cys_4$, $His/Cys_3$ residues underlined. The affinity purified recombinant protein was shown to be authentic Alfin1 protein by amino acid sequencing the amino terminal region of the protein. This sequence was identical to the sequence predicted from cloned cDNA as shown in Table 1 below.

TABLE 1

Recombinant Alfin1 amino acid sequence is identical with that predicted from the cDNA sequence.

|  | 10 | 20 | 30 | 40 | 50 |
|---|---|---|---|---|---|
| AA | TVEEVFSD | YKGRRAGLIK | ALTTDVEKFY | QLVDPEKENL | CLYGFPNET |
| cDNA | PRTVEEVFSD | YKGRRAGLIK | ALTTDVEKFY | QLVDPEKENL | CLYGFPNET |

Recombinant Alfin1 protein was purified and the amino acid sequence determined from thrombin cleaved protein as described in Bastola, D. R., Pethe, V. V. and Winicov, I. (1998) Alfin1, a novel zinc finger protein in alfalfa roots that binds to promoter elements in the salt inducible MsPRP2 gene. Plant Biol. 38, 1123–1135. Numbers indicate position of predicted amino acid from initiating methionine.

To identify DNA sequences that are recognized by Alfin1 protein, the purified Alfin1 protein was used in the "random DNA binding" assay (See: Rauscher III F. J., Morris J. F., Tournay O. E., Cook D. M., Curran T. *Binding of the Wilm's tumor locus* zinc finger protein to the EGR-1 consensus sequence. Science, 1990; 250, 1259–1262) and the bound DNA purified by four rounds of PCR amplification and binding, followed by cloning of the isolated sequences. Sequence analysis of the isolated clones (FIG. 2; SEQ ID NOS: 3–11) showed a consensus sequence in high affinity binding clones that was either GTGGNG or GNGGTG, confirming that Alfin1 was indeed a specific DNA binding factor that could potentially function in gene regulation. See FIG. 2 in which (A) shows Consensus sequences aligned from individual clones that bind Alfin1, which were isolated after four rounds of gel retardation assays coupled with PCR amplification of the bound sequences and (B) shows sequence elements similar to those cloned by PCR amplification of Alfin1 protein bound sequences that are found in the three MsPRP2 promoter fragments which bind Alfin1 protein in vitro.

Alfin1 was found to show a strong root specificity in its expression pattern. Therefore, as a DNA binding protein it would be a likely regulator for root specific gene expression. Three fragments from the 1552 bp root specific and salt inducible MsPRP2 promoter (FIG. 3; SEQ ID NO: 1) from alfalfa (See: Bastola, Pethe and Winicov, 1998, supra) were found to bind recombinant Alfin 1 protein in vitro, while a similar size control DNA fragment showed no DNA binding. See FIG. 3 in which DNA sequence of 1552 bp of the MsPRP2 promoter (SEQ ID NO: 1) is shown. (Underlined are: the translation start site at +1; the TATAA and CAAT sequences; the Tfil cleavage sites used for isolating Fragments 1, 2 and 3 for DNA binding experiments with recombinant Alfin1; the potential binding sites for Alfin1 as well as myc and myb transcription factors as discussed in the specification. (*) indicates that the potential binding site is found on the complementary DNA strand. This nucleotide sequence data has been assigned accession number AF028841 by GenBank, an international genetic information data base operated by the United States of America. The binding to the MsPRP2 promoter fragments was specific, could be inhibited by EDTA, was dependent on recombinant Alfin1 protein concentration and showed different affinities for each individual fragment. The DNA sequence of each fragment contained a variant of the G rich consensus binding sequence for Alfin1 protein that was identified in the random oligonucleotide selection as shown in FIG. 2 (SEQ ID NOS: 3–11) and could account for the observed binding in gel retardation assays. The correlation of this finding with both Alfin1 and MsPRP2 expression in roots and MsPRP2 inducibility by salt supported our hypothesis that Alfin1 could play a role in gene expression and root maintenance in our salt-toleratn plants and suggested a potential role for Alfin1 in strong root growth and development.

Since MsPRP2 expression is root specific in alfalfa, the newly characterized promoter region was of interest for identification of potential root specific DNA sequence elements. Although a number of root specific genes have been identified and several promoter regions have been shown to contain sequences for root specific expression of reporter genes (rev. Aeschbacher et al., 1994, supra), currently no consensus sequence specifying root specific expression has been identified. The 90 bp truncated cauliflower mosaic virus (CaMV) 35S promoter has been shown to contain a cis- regulatory element (TGACG) that interacts with the factor ASFI (See: Katagiri, F., Lam, E. and Chua, N-H. *Two tobacco DNA-binding proteins with homology to the nuclear factor CREB*. Nature 1989; 340, 727–730), but other root specific gene promoters evidently do not contain this sequence. The MsPRP2 promoter contains one 5'CGTCA 3' sequence (reverse of TGACG, the ASFI binding element) at position –1033, but contains none of the root specific elements implicated in ToBR7 gene regulation (See: Yamamoto, Y. T., Taylor, C. G., Acedo, G. N., Cheng, C-L and Conkling, M. A. *Characterization of cis- acting sequences regulating root-specific gene expression in tobacco*. Plant Cell, 1991; 3, 371–382). It was therefore necessary to determine whether Alfin1 binding sites represent a common element in promoter sequences for genes expressed in roots. A limited list of Alfin1 binding sequences in promoter regions from genes that are expressed in roots and salt stress are shown in Table 2, below, and demonstrates that all of these promoters contain some variation of the Alfin1 binding sequence. The CaMV 35S minimal promoter (–95 to –51) which is root specific (See: Lam, E., Benfey, P. N., Gilmartin, P. M., Fang, R-X and Chua, N-H. *Site-specific mutations alter in vitro factor binding and change promoter expression pattern in transgenic plants*. Proc. Natl. Acad. Sci., 1989; USA 86, 7890–7894), contains an Alfin1 binding site on the non-coding strand. The plant species represented in Table 2 are diverse and include both monocots and dicots. These results are consistent with our observation that Alfin1 sequence is widely conserved. In case of ToRB7, SbPRPP1 and PhyA promoters, Alfin1 binding sequences are located in regions that have been identified by deletion experiments as necessary for root expression (See: Yamamoto, Y. T., Taylor, C. G., Acedo, G. N., Cheng, C-L and Conkling, M. A. (1991) *Characterization of cis- acting sequences regulating root-specific gene expression in tobacco*. Plant Cell 3, 371–382). Several Alfin1 binding sequences are found in the promoter of another salt/drought inducible transcription factor Atmyb2 as well as the glutathione S transferase root specific genes induced by auxin or heavy metals such as copper and cadmium. Alfin1 binding sites are also abundant in the sucrose synthase promoters from different gene classes in potato and maize. All promoters of the tuber expressed patatin 1 multigene family contain conserved Alfin1 binding sites.

TABLE 2

Alfin1 binding sites found in salt/drought stress induced promoter sequences or root specific expression.
All sequences identified relative to the first ATG codon

| Gene | Sequence | GenBank Accession # |
| --- | --- | --- |
| MsPRP2 alfalfa root, cell wall salt stress | –299 5'GTGGGG3' –289 | AF028841 |
| HVA1 barley ABRE 2 root and shoot osmotic stress | –93 5'GTGGCG3' –87 | X78205 |
| Atmyb2 Arabidopsis root, petiole osmotic stress transcription factor | –559 5'GAAGTG3' –555<br>–461 5'GTGTGG3' –435<br>–222 5'GCCGTG3' –217 | D14712 |
| rab28 maize embryo, vegetative | –378 5'GTCGTGCAG3' –360 | X59138 |
| sh-1 maize root sucrose synthase | –974 5'GTGCCG3' –969<br>–855 5'GTGCTG3' –850<br>–825 5'GTTGTG3' –820<br>–749 5'GCTGTG3' –744<br>–617 5'GTGGGGTGG3' –609<br>–607 5'GTGGGGTGGGGGAG3' –609<br>–492 5'GTGTCG3' –487<br>–392 5'GTGGGG3' –387 | Werr et al. 1985 |
| sus3-65 potato root, stem sucrose synthase | –1502 5'GTGATG3' –1497<br>–1082 5'GTTGTG3' –1077<br>–891 5'GTGAAG3' –886<br>–804 5'GAAGTG3' –799<br>–165 5'GTGACGGTG3' –147 | U24088 |
| sus4-15 potato root, sucrose synthase | –903 5'GTGAGG3' –898 | U24087 |
| PS20 (class I)* potato tuber, patatin | –600 5'GAGGTG3' –595<br>–480 5'GTGAGG3' –475<br>–297 5'GAGGGGGTG3' –289<br>–160 5'GCGGTG3' –155<br>–146 5'GTGAGG3' –141 | Mignery et al. 1988 |

TABLE 2-continued

Alfin1 binding sites found in salt/drought stress induced
promoter sequences or root specific expression.
All sequences identified relative to the first ATG codon

| Gene | Sequence | GenBank Accession # |
|---|---|---|
| salT rice root, sheath osmotic stress | −1451 5'GTGCAG3' −1446<br>−843 5'GTGACG3' −828 | Z25811 |
| RCg2 rice root | 1445 5'GTGAAG3' 1450<br>1456 5'GCTGTG3' 1461 | L27210 |
| GOS9 rice root | −711 5'GGAGTG3' −706<br>−300 5'GACGTG3' −295<br>−204 5'GAGGTG3' −199 | X51909 |
| SbPRP1 soybean root | −942 5'GTGTGGGCGGAG3' −931<br>−213 5'GAGGTG3' −208 | I02746 |
| Osmotin tobacco mostly root, PRP prot. | −1447 5'GTGGTG3' −1442<br>−596 5'GTGGTG3' −591<br>−471 5'GTGGAG3' −466 | S68111 |
| OLP tobacco osmotin like, root | −296 5'GTGGCG3' −291 | Sato et al. 1996 |
| phyA tobacco trangenic root | −1133 5'GTGTGG3' −1128 | Adam et al. 1995 |
| TobRB7 tobacco root | −1809 5'GTGGAG3' −1804<br>−1751 5'GTGCGGTTG3' −1742<br>−1640 5'GGGGTG3' −1635<br>−1633 5'GTGTTG3' −1628<br>−1245 5'GTGTTG3' −1240<br>−724 5'GATGTGGAG3' −716<br>−377 5'GTGGAG3' −372 | Yamamoto et al. 1991 |
| HRGPnt3 tobacco root extensin | −1049 5'GTGCTG3' −1044<br>−917 5'GTGTCGGTG3' −909<br>−577 5'GGGGTG3' −580<br>−116 5'GTGGTG3' −111<br>−100 5'GTGTCG3' −95 | X13885 |
| Nt103-1 tobacco root GST | −928 5'GTGGTG3' −923 | X56268 |
| Nt103-35 tobacco root GST | −1096 5'GAGGTG3' −1091<br>−994 5'GAGGTGGAG3' −886<br>−644 5'GAGGTTGTG3' −633<br>−608 5'GTGGGG3' −603 | X56269 |
| CDeT27-45 resurrection plant | −703 5'GTGTGGGCG3' −695 | X69883 |

*Essentially the same sequences are found in the same order also for PAT21, PS3 and PS27 and to a lesser extent in PS7. Patatin Class II genes do not have this format, but have similar sequences on the non-coding strand.
Selection was made for the coding strand on basis of at least two adjacent triplets, one of which is GTG and the other is bordered by a G as defined by in vitro Alfin1 binding (Bastola, Pethe, and Winicov, 1998, supra). Additional sites were found on the non-coding strand in many of these gene promoters. Numbers in parentheses indicate GenBank accession numbers.
Adam, E., Kozma-Bognar, L, Dallmann, G. and Nagy, F. (1995) Transcription of tobacco phytochrome-A genes initiates at multiple start sites and requires multiple cis-acting regulatory elements. Plant Mol. Biol. 29, 983–993.
Mignery, G. A. Pikaard, C. S. and Park, W. D. (1998) Molecular characterization of the patatin multigene family of potato. Gene 62, 27–44.
Sato, F., Kitjima, S., Koyama, T. and Yamada, Y. (1996) Ethylene-induced gene expression of osmotin-like protein, a neutral isoform of tobacco PR-5, is mediated by the AGCCGCC cis-sequence. Plant Cell Physiol. 37, 249–255.
Werr, W., Frommer, W. B., Maas, C. and Starlinger, P. (1985) Structure of the sucrose synthase gene on chromosome 9 of *Zea mays* L. EMBO J. 4, 1373–1380.

These results indicate that Alfin1 protein could be a ubiquitous root specific transcription factor, involved in gene regulation under a wide variety of circumstances and could be used to enhance root growth for purposes of nutrient uptake, resistance to biotic and abiotic stress and general increase in plant yield under a variety of growth conditions. It is believed that Alfin1 is an essential transcription factor for gene expression in plants, especially in plant roots and expected that Alfin1 binding sequences function in gene promoters for Alfin1 protein regulation of gene expression controlled by these promoters and lead to enhanced mRNA accumulation from these genes. These predictions have been tested in transgenic plants that overexpress Alfin1.

Figure 4:
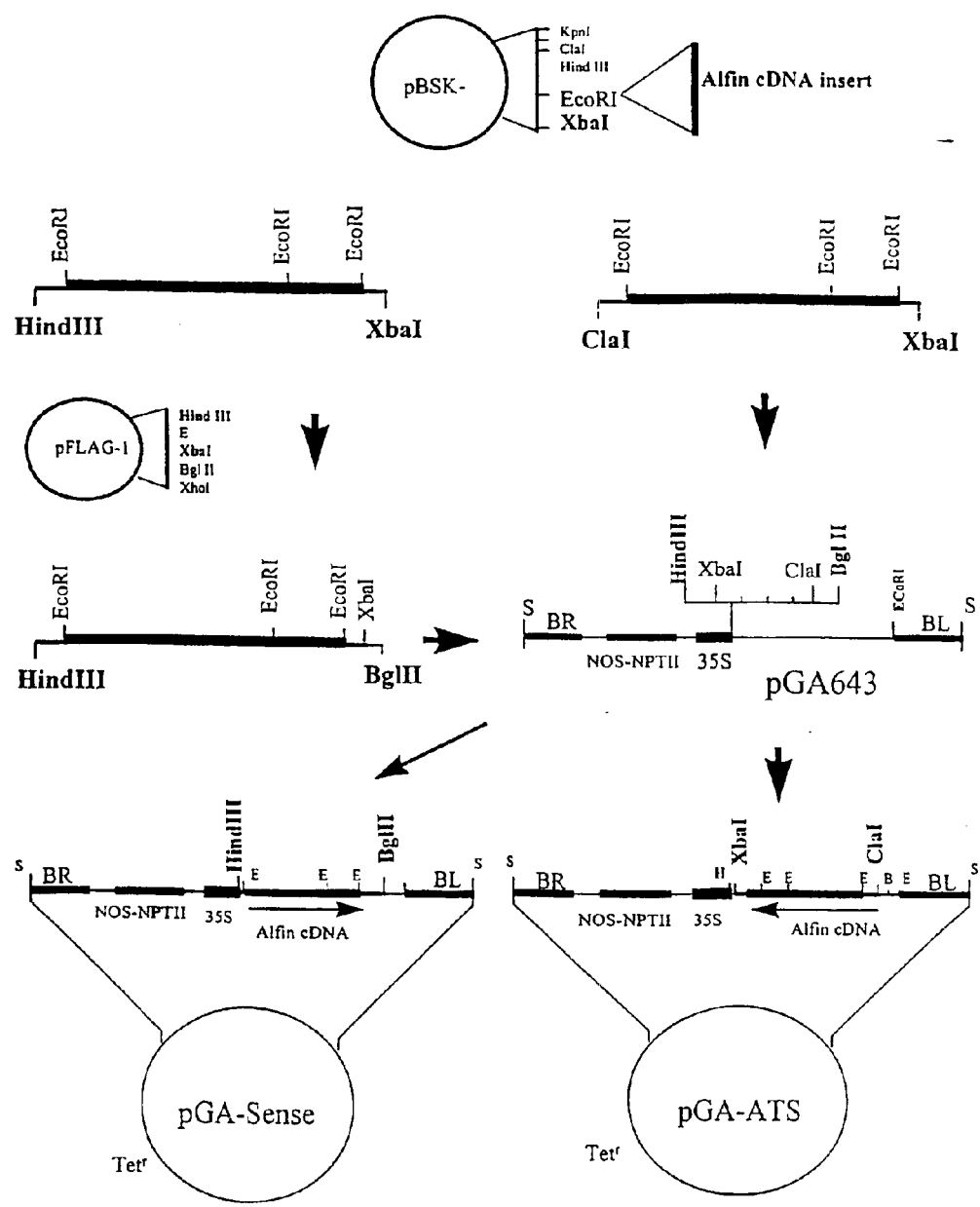
FIG. 4 shows the schematic representation of Alfin1 sense and antisense constructs used in transformation of alfalfa.

To test the effect of Alfin1 protein overexpression and underexpression on endogenous genes in alfalfa, Alfin1 was cloned in sense and antisense orientation and transformed in alfalfa leaf discs or immature ovaries with the constructs as shown in FIG. 4. (See: Winicov, I. and Bastola, D. R. (1999) *Transgenic over-expression of the transcription factor Alfin1* enhances expression of the endogenous MsPRP2 gene in alfalfa and improves salinity tolerance of the plants. Plant Physiol.).

Recombinant Plasmid Construction

Full length coding Alfin1 clone (pA50) consists of a 904 bp fragment of Alfin1 cDNA (GenBank accession # L07291) in pBluescript SK- (Stratagene). It contains a 30 bp 5' untranslated leader, a complete 771 bp coding sequence and 103 bp of the 3' untranslated region including the translation termination codon (Winicov 1993, supra). This cDNA fragment was cloned in the sense and antisense orientation in the multiple cloning site of the binary expression vector pGA643 as shown in FIG. 4.

To generate the sense construct, the 939 bp HindIII-XbaI fragment from pBluescript SK- was first subcloned in pFLAG (International Biotechnologies Inc., New Haven, Conn.), shown as PF-pA50, to gain a restriction site suitable for cloning the cDNA fragment in pGA643. The 957 bp HindIII-BglII fragment from PF-pA50, containing Alfin1 cDNA was then ligated to pGA643 in the multiple cloning site (MCS) 3' to the CaMV 35S promoter to give pGA-Sense. This clone would be predicted to give the complete Alfin1 coding transcript, but unlike the endogenous Alfin1 mRNA would carry additional sequences from the vector in its 3'UTR.

To generate the anti-sense construct (pGA-ATS), the 944 bp ClaI-XbaI fragment from pA50 (pBluescript SK-) was directly ligated into the pGA643 MCS site. Although another ClaI site is reported upstream to the MCS in pGA643, we found that only the ClaI site in MCS, indicated in FIG. 4, was cut by the enzyme.

The plasmids, pGA-Sense, pGA-ATS (antisense) and pGA643 (vector) were propagated in *Escherichia coli* strain MC1000 in presence of tetracycline. Freeze-thaw method was used in transforming *Agrobacterium tumefaciens* LBA 4404 with the recombinant binary plasmid. Transformed colonies were selected on 12 mg/l rifampicin and 6 mg/l tetracycline. Recombinant transformed colonies were identified by colony hybridization using the Alfin1 670 bp EcoRI fragment from pA50.

Plant Transformation

Alfalfa (*Medicago sativa* Regen S) salt-sensitive wild type parent plant #1 (Winicov, 1991, supra) leaves were transformed by *Agrobacterium* co-cultivation on SH growth medium, including 2 mg/l 2,4-D (2,4-dichlorophenoxyacetic acid) and 2 mg/l kinetin (See: Schenk, R. U. and Hildebrandt, A. C. *Medium and techniques for induction and growth of monocotyledonous and dicotyledonous plant cell cultures.* Can. J. Bot., 1972; 50, 199–204) and supplemented with 50 µM acetosyringone (Aldrich Chemical Co., St. Louis, Mo.) for 30 to 60 min at room temperature. One of the successful transformations was carried by co-cultivating *Agrobacterium* carrying the pGA-ATS with immature ovaries from the salt-tolerant alfalfa IW#9 (Winicov, 1991, supra). After two to six days on callus medium, the explants were transferred to selection medium (SH medium supplemented with 300 mg/l carbenicillin and 100 mg/l kanamycin) and incubated 3–4 weeks. The resistant calli were subcultured on the selection medium on a monthly basis. Plants were regenerated from the transformed calli on SH medium (without hormones) supplemented with 100 mg/l kanamycin. Plants with well defined shoots and roots were transferred to peat moss and subsequently to soil.

Callus cultures transformed with the sense construct showed improved growth on 171 mM NaCl and callus cultures transformed with the antisense construct were more sensitive to the same NaCl concentration as shown in Table 3 below. However, both transformants were able to grow well on normal Schenk and Hildebrandt (1972, supra) medium in continuous light. These results are consistent with our previous observations that our salt-tolerant calli showed an increase of Alfin1 transcription as measured by nuclear run-on experiments (See: Winicov, I. and Krishnan, M. *Transcriptional and post-transcriptional activation of genes in salt-tolerant alfalfa cells.* Planta, 1996; 200, 397–404) together with slightly increased steady state mRNA levels when the cells were grown on NaCl.

TABLE 3

Cell Growth of Transformed and Untransformed Alfalfa Cell Lines.

| Cell line | Kanamycin | Growth[a] (g wet weight/plate) 0 - NaCl | 171 mM NaCl |
|---|---|---|---|
| 1,1-untransformed | – | 5.49 ± 0.81 (n = 2) | 0.90 ± 0.47 (n = 3) |
| 1,1-t-vector(3)[b] | + | 4.34 ± 1.35 (n = 4) | 1.08 ± 0.20 (n = 6) |

TABLE 3-continued

Cell Growth of Transformed and Untransformed Alfalfa Cell Lines.

| Cell line | Kanamycin | Growth[a] (g wet weight/plate) 0 - NaCl | 171 mM NaCl |
|---|---|---|---|
| 1,1-t-Alfin1-sense(6)[b] | + | 5.06 ± 1.13 (n = 7) | 1.63 ± 0.38 (n = 9) |
| 1,5-untransformed | – | 5.36 ± 0.84 (n = 3) | 1.30 ± 0.48 (n = 3) |
| 1,5-t-vector(2)[b] | + | 3.83 ± 0.27 (n = 6) | 1.25 ± 0.27 (n = 6) |
| 1,5-t-Alfin1-antisense(4)[b] | + | 3.39 ± 0.91 (n = 7) | 0.93 ± 0.23[c] (n = 6) |

[a]Growth (mean ± SD) after four weeks on SH medium ± 171 mM NaCl, using an initial inoculum of about 0.1 g/callus and 5 calli/plate. n = number of plates.
[b]Number in parenthesis: number of different individual transformants included in test.
[c]Brown, dead callus.

Figure 5:
FIG. 5 shows alfalfa regenerated from Alfin1 sense and antisense transformed cell lines.
Figure 5:
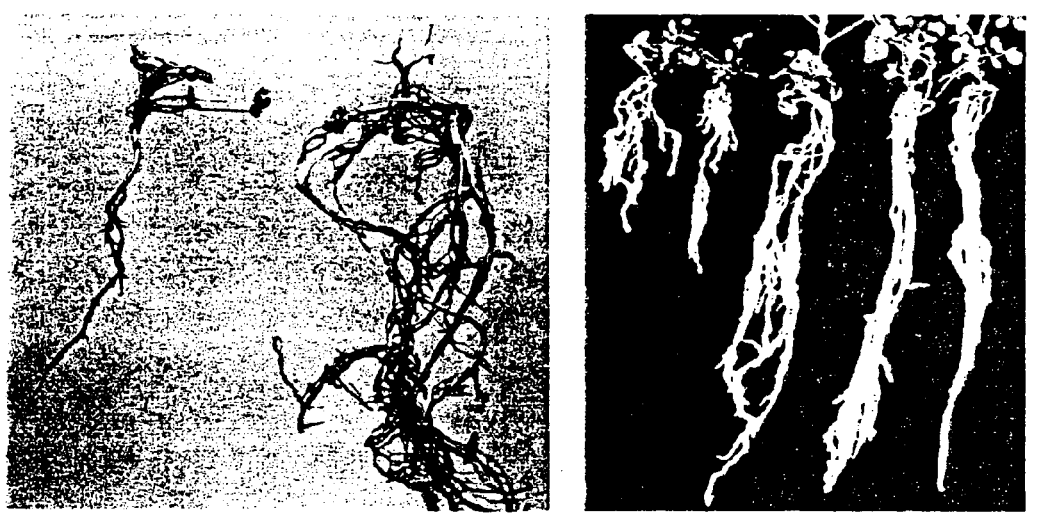

The role of Alfin1 in plant development became more apparent when plants were regenerated from the transgenic calli. Alfin1 expression appeared to be necessary for root production, since Alfin1 antisense expressing calli regenerated shoots but were deficient in root production and the few plants in which minimal root production was obtained, did not survive in soil for more than a few weeks. In contrast, calli containing vector only, or sense constructs regenerated plants that are vigorous, flower and set seed, despite the fact that the sense constructs are under the full CaMV 35S promoter and express the transgene in both roots and leaves. FIG. 5 shows a composite picture of: 1) two large plants expressing Alfin1 in the sense orientation; 2) the only small antisense plant that survived in soil for a few months; and 3) some root-less antisense plants after several months on regeneration medium. It is clear from these results that Alfin1 expression is essential for root development and plant growth in soil and supports the belief that Alfin1 protein is a ubiquitous root specific transcription factor.

Figure 6A:
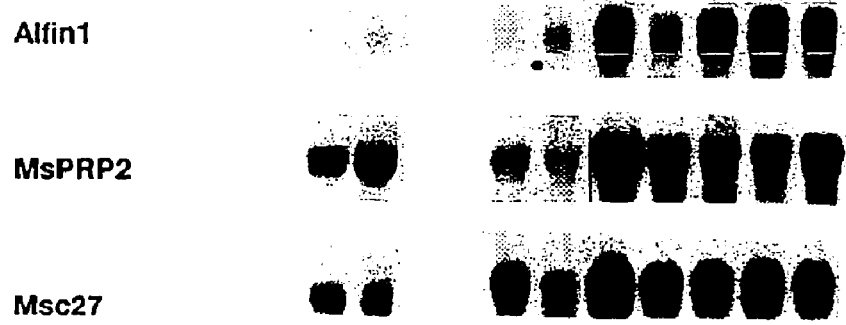
FIG. 6 shows northern blot analysis of Alfin1 and MsPRP2 expression in transgenic calli and plants from Alfin1 sense transformants.
Figure 6B:
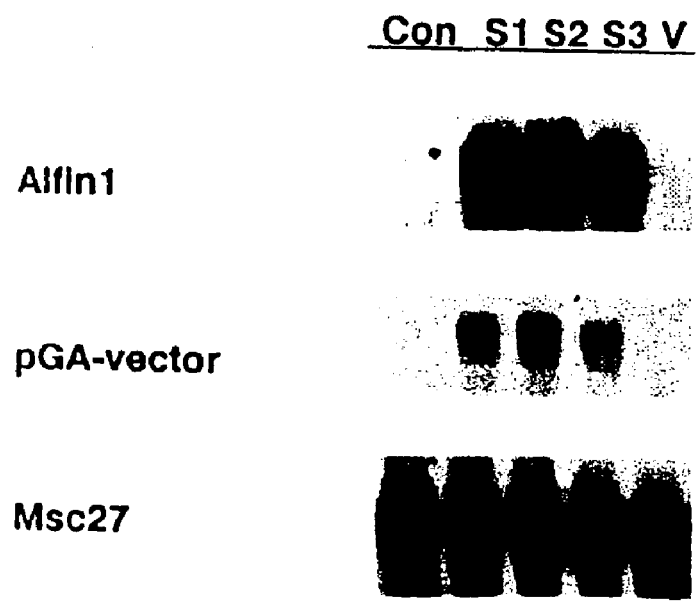
Figure 6C:
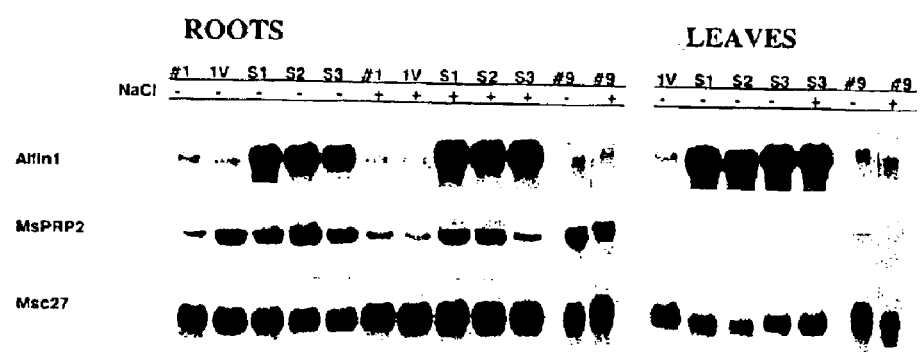

Since our DNA binding experiments with recombinant Alfin1 showed specific binding to the MsPRP2 promoter, MsPRP2 mRNA levels were measured in transgenic calli and plants overexpressing Alfin1. (See: Winicov and Bastola, 1999, supra). In transgenic calli and plant roots Alfin1 overexpression was accompanied by increased levels of MsPRP2 mRNA as shown in FIGS. 6A and 6C in which the Callus. data shows, in Lanes 1 and 2: RNA isolated from untransformed salt-tolerant callus grown ±171 mM NaCl for four weeks. Lane 3: RNA isolated from untransformed salt-sensitive callus. Lane 4: RNA isolated from salt-sensitive calius transformed with pGA vector. Lanes 5–8: RNA isolated from salt-sensitive callus transformed with Alfin1 sense construct; S1, S2, S4 and S6 are independently transformed lines. Lane 9: RNA isolated from S2 transformed callus grown in 171 mM NaCl. Each lane contained 10 µg total RNA.

Each blot was hybridized sequentially with the following probes: Alfin1, large EcoRI fragment (FIG. 1); MsPRP2, the carboxyterminal and 3' untranslated region fragment (Winicov and Deutch, 1994, supra), Msc27, fragment of a constitutively expressed alfalfa gene. In each cell line transformed with Alfin1 sense construct, Alfin1 overexpression is accompanied by increased levels of MsPRP2 mRNA FIG. 6B shows that plants transformed with Alfin1 express the transgene as monitored with the PGA-vector tag in Alfin1 mRNA FIG. 6C shows Alfin1 and $M_sPRP$ expression in Roots and Leaves. Total RNA was isolated from roots and leaves of the same plant. #1 is control salt-sensitive plant, IV is empty vector transformed plant, S1, S2, and S3 are plants transformed with Alfin1 sense construct and regenerated from transformed callus. #9 is a salt-tolerant control plant. Each blot was hybridized sequentially with the following probes: Alfin1, large EcoRI fragment (FIG. 1 (SEQ ID NO: 2): MsPRP2, the carboxyterminal and 3' untranslated region fragment; Msc27, fragment of a constitutively expressed alfalfa gene to minotor for loading of each lane. Each lane contained 10 µg of total RNA. These results demonstrate that increased expression of Alfin1 led to increased levels of mRNA accumulation from the endogenous MsPRP2 gene, consistent with Alfin1 role in MsPRP2 transcriptional activation. However, this transcriptional activation was root specific, since leaves from the same transgenic plants showed increased Alfin1 mRNA levels without a concomitant increase in MsPRP2 transcripts, implying an interaction between Alfin1 and other gene product(s) present in the root for MsPRP2 transcriptional activation. Because Alfin1 contains a very acidic domain as shown in FIG. 1B, just upstream from the postulated zinc finger region, Alfin1 could interact also with additional lfactors in binding to DNA. Interestingly, the MsPRP2 promoter sequence shown in FIG. 3 (SEC ID NO: 1) contains numerous myc and myb recognition sites, several of which lie in close proximity to the Alfin1 binding sites, suggesting the possibility of interactions with these transcription factors, similar to those already shown for myc and myb in *Arabidopsis* (Abe et al., 1997, supra).

The results obtained support a central role for Alfin1 in root development and root specific gene expression. Additional experiments support the role of Alfin1 overexpression in enhanced root growth under normal and stress conditions. Plants compared under the test conditions include the salt-sensitive parent #1 from which leaves were used for transformation experiments, transgenics transformed with the vector alone and transgenics which express high levels of Alfin1. Controls also include salt tolerant plant #9, which when transformed with the antisense construct that could nor develop roots. For measurement of root growth and salt tolerance of the Alfin1 overexpressing transgenic plants, rooted cuttings were established in containers in PERLITE (Paxlite, pax Co., Salt Lake City, Utah) from the above plants and watered daily with a regimen of water to flush out any accumulation of salts, followed by thorough watering with ¼ strength Hoagland's solution as described in (Winicov, 1991, supra). Preliminary results of plant root and shoot growth measurements in (cm) length as well total mass by weight (g) after four weeks confirmed our theory. As shown in Table 4, below, plants transformed with Alfin1 show enhanced root growth (438% above parental control) as the postulated role of Alfin1 in root development would predict. Current experiments extended these measurements to other individually regenerated Alfin1 containing transgenic plants.

TABLE 4

Enhanced root growth by transgenic Alfalfa overexpressing Alfin1

| Plant | Root length[a] (cm) | % | Root wt.[a] (g) | % |
|---|---|---|---|---|
| Experiment 1 (28 days) | | | | |
| #1 Parent | 10.3 ± 4.3 (n = 3) | 100 | 0.32 ± 0.23 (n = 3) | 100 |
| #1 + vector transformed | 13.2 ± 6.5 (n = 3) | 128 | 0.65 ± 0.50 (n = 3) | 203 |
| #1 + Alfin1-1 sense transformed | 19.0 ± 1.3 (n = 3) | 184 | 1.39 ± 0.83 (n = 3) | 438 |
| #9-control salt-tolerant[b] | 14.0 ± 6.2 (n = 11) | 136 | 0.55 ± 0.37 (n = 11) | 172 |

TABLE 4-continued

Enhanced root growth by transgenic Alfalfa overexpressing Alfin1

| Plant | Root length[a] (cm) | % | Root wt.[a] (g) | % |
|---|---|---|---|---|
| Experiment 2 (20 days) | | | | |
| #1 Parent | 6.4 ± 2.6 (n = 8) | 100 | 0.35 ± 0.18 (n = 8) | 100 |
| #1 + vector transformed | 9.5 ± 2.8 (n = 5) | 148 | 0.35 ± 0.19 (n = 5) | 100 |
| #1 + Alfin1-1 sense transf. | 19.4 ± 2.5 (n = 21) | 303 | 1.87 ± 0.91 (n = 21) | 534 |
| #1 + Alfin1-2 sense transf. | 19.3 ± 1.9 (n = 11) | 302 | 1.09 ± 0.38 (n = 11) | 311 |
| #1 + Alfin1-3 sense transf. | 17.7 ± 4.5 (n = 6) | 277 | 1.06 ± 0.35 (n = 6) | 303 |
| #9-control salt-tolerant[b] | 17.5 ± 3.0 (n = 15) | 273 | 0.85 ± 0.41 (n = 15) | 243 |

[a]All measurements expressed as M ± SD of replicate cuttings of individual plants after growth for the indicated time. Alfin1-1, Alfin1-2, Alfin1-3 are three different plants regenerated from different transformation events. Average daytime temperatures in the greenhouse were warmer in Exp. 2.
[b]This is a salt-tolerant plant selected in tissue culture on 171 mM NaCl and regenerated as previously described (Winicov, 1991, supra).

Comparative root growth experiments with cuttings of the above described plants also was carried out in soil, using equal size pots under greenhouse conditions and a regular watering schedule. While growth rates can vary between PERLITE and soil, the relative rates of root and shoot growth between the various test plants and controls remained substantially the same.

It was also believed that transgenic plants overexpressing Alfin1 with improved root development would also show improved salt-tolerance. Salt-tolerance was measured as described previously (See: Winicov, I. *Characterization of salt tolerant alfalfa* (*Medicago sativa* L *plants regenerated from salt tolerant cell lines*. Plant Cell Reports, 1991; 10, 561–564.). The plants were established in Conetainers as above, cut back and divided into two groups with at least five replica cuttings of each individual regenerated plant in each group. Group I (control, or 0%0% NaCl), was treated with the regimen of water and ¼ strength Hoagland's as described above. Group II was treated with the Hoagland's solution containing 0.5% or more NaCl. Tolerance is expressed as number of survivors per number of replica plants in each group after treatment. Plant growth is quantitated by harvesting the shoots of surviving plants as the end of each experiment and calculated as the average total shoot fresh weight per plant in each group. This value represents the net increase in mass during the test period under the given salt conditions.

Although increased root growth in the Alfin1 overexpressing plants under normal conditions together with more vigorous shoot growth was expected, the salt-stress test may not accurately predict salt-tolerance capabilities of Alfin1 overexpression under tissue specific regulatory conditions. Our current transgenic plants overexpressing Alfin1 under the 35S promoter express this gene product inappropriately in the leaves which under stress conditions may be influenced adversely by the inappropriate presence of this gene product. However, tissue specific regulation of Alfin1 function seems to mostly override this potential problem. Thus accurate assessment of enhanced biotic and abiotic resistance of the Alfin1 overexpressing transgenics may be even improved by construction of new transgenics in which Alfin1 expression will be more tightly under the control of a root specific promoter. Such a promoter, which is the MsPRP2 promoter shown in FIG. 3 (SEQ ID NO: 1) (has been cloned), for construction of root specific Alfin1 transgene and to direct additional Alfin1 expression to roots. Essentially, the 35S promoter for the sense and antisense constructs shown in FIG. 4 is replaced with the 1552 bp promoter of MsPRP2 and the transformation repeated as before. Since this promoter also binds Alfin1 protein as demonstrated by our current tests, it is believed that these root specific Alfin1 transgenics will perform even better than the Alfin1 sense transgenics under the 35S promoter shown by the current results obtained.

The Alfin1 transgene can be under the control of the CaMV 35S promoter as described. In addition the Alfin1 transgene can be placed under the control of the full or partial 1500 bp MsPRP2 promoter FIG. 3 (SEQ ID NO: 1) (Bastola, Pethe, and Winicov, 1998, supra) using appropriate restriction sites in the promoter region and Alfin1 sense construct described in FIG. 4 to construct a new Alfin1 expression vector for creation of transgenic plants overexpressing the Alfin1 protein.

The full or partial MsPRP2 promoter sequence (Bastola, Pethe and Winicov, 1998, supra) can be also used by itself or in conjunction with other promoter sequence elements to construct new composite promoter regulatory sequences, (using routine molecular biology techniques that re-ligate specific DNA fragments cut by restriction enzymes) that would give root specific and/or Alfin1 protein regulated expression to other genes transferred into plants.

The Alfin1 protein binding sequences (Bastola, Pethe and Winicov, 1998, supra) can be also used by themselves, as concatenates or in conjunction with other promoter sequence elements to construct new composite promoter regulatory sequences (using routine molecular biology techniques that re-ligate specific DNA fragments cut by restriction enzymes) that would give root specific and/or Alfin1 protein regulated expression to other genes transferred into plants.

It is believed that introduction of Alfin1 binding sites in appropriate promoter contexts could lead to regulation of additional genes by Alfin 1.

It is further believed that any molecular interference with Alfin1 (or its analogue) expression or function in plant roots by any compound or molecule will inhibit plant root development, plant growth and, as such, effectively act as herbicide.

Finally, the increased root growth by plants overexpressing Alfin1 increases plant survival under saline conditions and continues to provide growth under conditions where the parent plants and plants transformed with the empty vector produce a minimal shoot yield as shown. See: Tables 5A, 5B, 6 and 7 below.

TABLE 5A

Enhanced Root Growth by Transgenic Alfalfa Overexpressing Alfin1 in Presence of 171 mM NaCl.

| Plant | Root length[a] (cm) | % | Root wt.[a] (g) | % |
|---|---|---|---|---|
| #1 Parent | 3.8 ± 0.8 (n = 7) | 100 | 0.20 ± 0.12 (n = 7) | 100 |
| #1 + Alfin1-1 sense transf. | 15.0 ± 3.5 (n = 7) | 395 | 0.78 ± 0.39 (n = 7) | 350 |
| #1 + Alfin1-2 sense transf. | 11.0 ± 4.8 (n = 7) | 289 | 0.55 ± 0.40 (n = 7) | 275 |
| #9-control salt-tolerant[b] | 7.1 ± 3.5 (n = 7) | 189 | 0.34 ± 0.17 (n = 7) | 170 |

[a]All measurements expressed as M ± SD of replicate cuttings of individual plants. The rooted cuttings (root size approximately 1 cm) were planted in Conetainers with PERLITE and watered with ¼ strength Hoagland's solution for 6 days. From day 7 until day 20 watering continued with the Hoagland's solution containing 171 mM NaCl. Shoot death occurred from day 11 through day 20 as depicted in Table 2. All roots were measured on day 20.
[b]This is a salt tolerant plant selected in tissue culture on 171 mM NaCl and regenerated as previously described (Winicov, 1991 supra).

TABLE 5B

Shoot survival by transgenic Alfalfa overexpressing Alfin1 in 171 mM NaCl.

| Plant | Surviving on Day 11[a] | % | Surviving on Day 11[a] | % |
|---|---|---|---|---|
| #1 Parent | 5/7 | 71 | 1/7 | 14 |
| #1 + Alfin1-1 sense transf. | 6/7 | 86 | 3/7 | 43 |
| #1 + Alfin1-2 sense transf. | 6/7 | 86 | 5/7 | 71 |
| #9-control salt-tolerant[b] | 7/7 | 100 | 6/7 | 86 |

[a]All measurements expressed as M ± SD of replicate cuttings of individual plants. The rooted cuttings (root size approximately 1 cm) were planted in Conetainers with PERLITE and watered with ¼ strength Hoagland's solution for 6 days. From day 7 until day 20 watering continued with the Hoagland's solution containing 171 mM NaCl. Shoot death occurred from day 11 through day 20 as depicted in Table 2. All roots were measured on day 20.
[b]This is a salt tolerant plant selected in tissue culture on 171 mM NaCl and regenerated as previously described (Winicov, 1991 supra).

TABLE 6

Growth Properties of Alfin1 'sense' transformed plants on 128 mM NaCl.

| Plant | Survival | New leaf growth[a] (g/plant) | % |
|---|---|---|---|
| #1 (parent) | 4/5 | 0.56 ± 0.32 | 100 |
| #1 + vector | 4/5 | 0.42 ± 0.32 | 75 |
| #1 + sense-1 | 7/7 | 1.40 ± 0.17 | 250 |
| #1 + sense-2 | 7/7 | 1.85 ± 0.23 | 330 |
| #1 + sense-3 | 3/3 | 1.45 ± 0.32 | 259 |
| IW9[b] | 7/7 | 1.10 ± 0.18 | 196 |

[a]Rooted multiple cuttings from each plant were established in Conetainers in PERLITE for six weeks and grown on ¼ strength Hoagland's solution. All shoots were then cut back to the crown. Growth was continued from that point on ¼ strength Hoagland's supplemented with 128 mM (0.75%) NaCl. The newly regrown shoots were harvested and weighed after 17 days. Weight in g (M ± SD).
[b]Salt-tolerant plant regenerated after selection in tissue culture from parent plant #1 (Winicov, 1991 supra).

Further tests demonstrating that plants over-expressing Alfin1 outperformed the parent plants and plants transformed with the empty vector in short yield under test conditions, which was consistent with their enhanced root development.

The results are shown below in Table 7.

TABLE 7

Shoot growth properties of Alfin1 'sense' transformed plants on ¼ strength Hoagland's solution.

| Plant | Survival | New leaf growth[a] (g/plant) | % |
|---|---|---|---|
| #1 (parent) | 5/5 | 0.42 ± 0.10 | 100 |
| #1 + vector | 5/5 | 1.07 ± 0.61 | 254 |
| #1 + sense-1 | 7/7 | 2.36 ± 0.33 | 562 |
| #1 + sense-2 | 5/5 | 1.77 ± 0.74 | 421 |
| #1 + sense-3 | 3/3 | 1.60 ± 0.71 | 381 |
| IW9[b] | 7/7 | 1.41 ± 0.35 | 335 |

[a]Rooted multiple cuttings from each plant were established in Conetainers in PERLITE for six weeks and grown on ¼ strength Hoagland's solution. All shoots were then cut back to the crown. Growth was continued from that point on ¼ strength Hoagland's. The newly regrown shoots were harvested and weighed after 17 days. Weight in g (M ± SD).
[b]Salt-tolerant plant regenerated after selection in tissue culture from parent plant #1 (Winicov, 1991 supra).

From the foregoing it is readily apparent that a new and useful embodiment of the present invention has been herein described and illustrated which fulfills all of the aforestated objects in a remarkably unexpected fashion. It is, of course, understood that such modification, alterations and adaptations as may readily occur to the artisan confronted with this disclosure are intended within the spirit of this invention which is limited only by the scope of the claims appended hereto.

What is claimed is:

1. An isolated Alfalfa MsPRP2 promoter comprising SEQ ID NO:1.

\* \* \* \* \*

UNITED STATES PATENT AND TRADEMARK OFFICE
CERTIFICATE OF CORRECTION

PATENT NO. : 6,936,708 B1
DATED : August 30, 2005
INVENTOR(S) : Ilga Winicov

It is certified that error appears in the above-identified patent and that said Letters Patent is hereby corrected as shown below:

Title page,
Item [75], Inventor, "Scottdale" should read -- Scottsdale --;
Item [56], References Cited, OTHER PUBLICATIONS,
"Oommenn" should read -- Oommen --;
"Wout Boejan" reference, "supperroot" should read -- superroot --;
"Raul B. Larson" should read -- Paul B. Larsen --;
"Paul B. Larsen" reference, "1201-1214" should read -- 1207-1214 --;
"Ce Deutch" should read -- C.E. Deutch --;
"C.E. Deutch" reference, "1995, (Abstract Only)" should read -- 1995, 27:411-418 (Abstract Only) --;
"C.E. Deutch" reference, "Plants Plant Physiology" should read -- Plants, Plant Physiology --;
"Dhundy R. Bastola et al." reference, "elements in ;the salt" should read -- elements in the salt --;
"Yuri T. Yamamoto" reference, "vol. 4985 (Abstract Only)" should read -- vol. 250 (Abstract Only) --;
"E. Adam" reference, "elements, plant Mol Biol." should read -- elements, Plant Mol Biol. --;
"GA Mignery" should read -- G.A. Mignery --.

Column 2,
Line 45, "Winicov, I. and Deurch, C.E." should read -- Winicov, I. and Deutch, C.E. --.

Column 4,
Line 21 Table 1, "Plant Biol. 38" should read -- Plant Mol. Biol. 38 --.

Column 5,
Line 10, "salt-toleratn" should read -- salt-tolerant --.

Column 7,
Line 39 Table 2, "Mignery, G.A. Pikaard, D.S. and Park, W.D. (1990)" should read -- Mignery, G.A., Pikaard, C.S. and Park W.D. (1988) --.

Column 12,
Line 39, "(control, or 0%0% NaCl)" should read -- (control, or 0% =NaCl) --.

UNITED STATES PATENT AND TRADEMARK OFFICE
CERTIFICATE OF CORRECTION

PATENT NO. : 6,936,708 B1
DATED : August 30, 2005
INVENTOR(S) : Ilga Winicov

It is certified that error appears in the above-identified patent and that said Letters Patent is hereby corrected as shown below:

Column 14,
Line 6 (Table 5B) 4th Column Heading, "Day 11$^a$" should read -- Day 20$^a$ --.

Signed and Sealed this

Fourteenth Day of March, 2006

JON W. DUDAS
*Director of the United States Patent and Trademark Office*

SEQUENCE LISTING

<160> NUMBER OF SEQ ID NOS: 11

<210> SEQ ID NO 1
<211> LENGTH: 1613
<212> TYPE: DNA
<213> ORGANISM: Medicago sativa

<400> SEQUENCE: 1

```
ttttataaat atttaagctt gataataatt ttgcgatcta tatataagcc cactaccaat     60
ttaaaattat atatatatat atatatatat atatatatat aataattttt atttaccaat    120
ttaaaattat atatatatat atatatatat atatatatat aataattttt attatattta    180
ttacgttgat ggtaaaaaaa taatatataat ttgttaccat ttaaaagtca taaatatagt    240
acaatccaac cctttgagag gttaatgtgt gtgcggattt tctagataaa caaggygcca    300
ttcacgattc ttcttggtgc agcttggaga accctatcct gggcttggaa gatttacttc    360
ttgttgatgc ttctagagta cagctcctta aggctgtagt ctagttttt ttttcatcct    420
tcctaccaaa aaaaaaaaag tcataaatat agtttataca tataacttta ataaaaataa    480
aaaaatttca tccctaaaaa catagtagaa atttcataaa aaaaatattg tttataattt    540
acatgccgtt acggtaaaaa atggataaat tgggtatgga gtactagtaa ttaataaggt    600
tcattggtta aaaaaactaa aaaataattt ctctcctgat ttatatgaaa tgacattttt    660
ttggaacatg aagggtattg atttttacca ccttttacac ctttcaaagc cattcaagga    720
tgaatataga ttttttgggcg atcaaacaca agaatcatta cgataacatg cttatacata    780
ccccgtcaat cttcttttt ttacccaata aacattgaaa tgttgcttct ttcgttaagc    840
ataaaaacat caaagtctag caaaatgttg tttttgcgat gacacatttc atatagttta    900
aaggatgcat gattcgatta caaaaacaaa atactaataa ttctagcaca aagtttaaag    960
caatattata aagcttcata gcatgtggat attcatttag aaatatagat tagattgccc   1020
ctttcatcac gggtctaaca gcaccacttg tcactacatg tcaaaaatgt cctctagtac   1080
agcaccgctt tttacttgat tccccttgtc catgcatgaa aaaaatcaaa acaatatttg   1140
gacacacaaa cttgcccca cttttccttt tctttctgcc ctagtttgtt tgagactcat   1200
attgatcaaa tttggctatg aattcaaaca aaaaattcac tctacccatt gcatgtgtgg   1260
ggcccacata taaatccatg aaggatttca atgtccatcc aagtcaatga ttcaacatat   1320
ataacattga ataatttaat tccaatttgc agtattatga tttagattga ttgctgcaat   1380
acggtccgtg aatgtgatca ctcacgagaa agaggtatca aaatttcaag gtattttatt   1440
tatttttaac aaataaaatt tcaaggtctt gttcaccata taaacctcct cactcacacc   1500
caattctctt aagtgtatga cttcatagta cactacacta ctttctttga aacatggcta   1560
actatgctct agccaatgtt ttcatccttc tcttgaactt gagtaccttta ctc         1613
```

<210> SEQ ID NO 2
<211> LENGTH: 904
<212> TYPE: DNA
<213> ORGANISM: Medicago sativa -continued

```
<400> SEQUENCE: 2
gaattccctt gacttttgtt gaaattgagg atggaaggaa tggcacagca cccagtacct      60
cgaactgttg aagaagtttt tagcgattac aaaggcagac gcgccggttt gatcaaagct     120
ctcactactg acgttgaaaa gttttaccag ctcgtcgatc ccgaaaagga gaatttgtgc     180
ctctatgggt ttccaaatga acatgggaa gtgaacttgc ctgttgagga agtgcctcct     240
gaacttcccg agccagcatt gggtataaac tttgctcggg atggaatgca ggagaaggac     300
tggttatcac tggttgcagt tcacagtgac tcatggctgc tcgctgttgc tttctatttt     360
ggtgcccgct ttggatttgg taagaatgat aggaaaaggc tttttcagat gataaatgat     420
ctgcccacag tctttgagct tgcaacagga actgctaagc aatcaaagga ccaactgact     480
gctcacaaca atggtagcaa tagcaaatac aaatcaagtg aaagtcccg ccagtctgaa      540 tcccagacca agggtgtgaa gatgtctgca ccggtcaaag aagaggttga cagtggagaa     600
gaagaggaag aagatgatga tgaacaaggt gcaacctgtg gtgcttgtgg tgataattat     660
ggcaccgatg aattctggat ctgttgtgat atgtgcgaga atggttcca tggtaaatgt      720 gttaaaatta ctcctgccaa ggctgaacac atcaagcaat acaagtgccc tggctgcagt     780
atcaagaagc aagaattgg atagctctga acgtttggac cattagcggg caagattaaa      840
atgtttgtta gcatttctgt aagtgaaacc attgttgtct gcatagtcac ttaaagggaa     900
ttcc                                                                  904

<210> SEQ ID NO 3
<211> LENGTH: 29
<212> TYPE: DNA
<213> ORGANISM: Medicago sativa

<400> SEQUENCE: 3
gacggctggg ggaaagtgag cggtggccc                                        29

<210> SEQ ID NO 4
<211> LENGTH: 29
<212> TYPE: DNA
<213> ORGANISM: Medicago sativa

<400> SEQUENCE: 4
gacgcaaagg gggtggggac ggcgctttt                                        29

<210> SEQ ID NO 5
<211> LENGTH: 29
<212> TYPE: DNA
<213> ORGANISM: Medicago sativa

<400> SEQUENCE: 5
gacgcaaagg gggtggggac ggcgctttt                                        29

<210> SEQ ID NO 6
<211> LENGTH: 29
<212> TYPE: DNA
<213> ORGANISM: Medicago sativa

<400> SEQUENCE: 6
gacgggtagg gtgtgggggg tgttttatt                                        29

<210> SEQ ID NO 7
<211> LENGTH: 29
<212> TYPE: DNA
<213> ORGANISM: Medicago sativa
```

-continued

```
<400> SEQUENCE: 7
gacggggata ggtgaggtgg agggacaat                                              29

<210> SEQ ID NO 8
<211> LENGTH: 29
<212> TYPE: DNA
<213> ORGANISM: Medicago sativa

<400> SEQUENCE: 8
gacggcagaa gggagaaacg tggagaatc                                              29

<210> SEQ ID NO 9
<211> LENGTH: 29
<212> TYPE: DNA
<213> ORGANISM: Medicago sativa

<400> SEQUENCE: 9
gacggcggga aggagtgtgg tagagagcc                                              29

<210> SEQ ID NO 10
<211> LENGTH: 27
<212> TYPE: DNA
<213> ORGANISM: Medicago sativa

<400> SEQUENCE: 10
gacgaaggaa ggacggcagc gtgttgc                                                27

<210> SEQ ID NO 11
<211> LENGTH: 29
<212> TYPE: DNA
<213> ORGANISM: Medicago sativa
<220> FEATURE:
<221> NAME/KEY: misc_feature
<222> LOCATION: (9)..(9)
<223> OTHER INFORMATION: n = A, C, T or G
<220> FEATURE:
<221> NAME/KEY: misc_feature
<222> LOCATION: (13)..(13)
<223> OTHER INFORMATION: n = A, C, T or G
<220> FEATURE:
<221> NAME/KEY: misc_feature
<222> LOCATION: (15)..(15)
<223> OTHER INFORMATION: n = A, C, T or G

<400> SEQUENCE: 11
gacgaaaant tanangtgta ggtgggact                                              29
```